(12) United States Patent
Morrow et al.

(10) Patent No.: US 7,900,269 B2
(45) Date of Patent: *Mar. 8, 2011

(54) NO-SLIP PROTECTOR

(75) Inventors: David Morrow, Farmington Hills, MI (US); Jesse Hubbard, New York, NY (US)

(73) Assignee: Warrior Sports, Inc., Warren, MI (US)

( * ) Notice: Subject to any disclaimer, the term of this patent is extended or adjusted under 35 U.S.C. 154(b) by 45 days.

This patent is subject to a terminal disclaimer.

(21) Appl. No.: 11/928,029

(22) Filed: Oct. 30, 2007

(65) Prior Publication Data

US 2008/0040829 A1    Feb. 21, 2008

Related U.S. Application Data

(63) Continuation of application No. 10/187,680, filed on Jul. 2, 2002, now Pat. No. 7,356,849.

(51) Int. Cl.
*A41D 13/00* (2006.01)

(52) U.S. Cl. ............................................................ 2/16

(58) Field of Classification Search ................ 2/16, 455, 2/267, 22, 24, 465; 602/62, 63, 26; 128/881
See application file for complete search history.

(56) References Cited

U.S. PATENT DOCUMENTS

| | | |
|---|---|---|
| 1,277,706 A | 9/1918 | Dorfman |
| 3,561,436 A | 2/1971 | Gaylord, Jr. |
| 3,648,291 A | 3/1972 | Pankers |
| 3,789,842 A | 2/1974 | Froimson |
| 3,911,497 A | 10/1975 | Lewis, Jr. et al. |
| 4,014,327 A | 3/1977 | Spiro |
| 4,027,666 A | 6/1977 | Marx |
| 4,048,991 A | 9/1977 | Marx |
| 4,120,052 A | 10/1978 | Butler |
| 4,150,442 A | 4/1979 | Boone |
| 4,198,708 A | 4/1980 | Fugere et al. |
| 4,422,183 A | 12/1983 | Landi et al. |
| 4,441,211 A | 4/1984 | Donzis |

(Continued)

OTHER PUBLICATIONS

STX Lacrosse Catalog 2000; Elbow Pad.

(Continued)

*Primary Examiner* — Tejash Patel
(74) *Attorney, Agent, or Firm* — Warner Norcross & Judd LLP

(57) ABSTRACT

A protector for protecting a wearer is disclosed herein. The protector includes a protection element extending along an axis between first and second ends. The protection element has an inner surface for at least partially contacting a wearer, an outer surface opposite the inner surface, and an outer edge. The protector also includes at least one elastic band arrangement connected to the outer edge at two places and overlaying the inner surface and being operable to allow at least a portion of the wearer to be received between the at least one elastic band and the inner surface. The protector also includes at least one friction element coupled to the inner surface and discreet from the at least one elastic band. The at least one friction element defines a greater coefficient of friction than the inner surface and is thereby more operable to minimize movement of the protection element relative to the wearer than the inner surface. The at least one friction element and the at least one elastic band are spaced from one another along the axis such that either the at least one friction element or the at least one elastic band can tend to limit sliding movement of the protector as the portion of the wearer expands or contracts during use.

24 Claims, 2 Drawing Sheets

U.S. PATENT DOCUMENTS

| | | | | |
|---|---|---|---|---|
| 4,453,271 | A | 6/1984 | Donzis | |
| 4,467,475 | A | 8/1984 | Gregory et al. | |
| 4,484,361 | A | 11/1984 | Leighton et al. | |
| 4,513,449 | A | 4/1985 | Donzis | |
| 4,590,622 | A | 5/1986 | Wolfe et al. | |
| 4,642,814 | A | 2/1987 | Godfrey | |
| 4,722,099 | A | 2/1988 | Kratz | |
| 4,922,929 | A | 5/1990 | DeJournett | |
| 4,953,569 | A * | 9/1990 | Lonardo | 128/892 |
| 4,985,931 | A | 1/1991 | Wingo, Jr. | |
| 5,159,715 | A | 11/1992 | Jurga et al. | |
| 5,168,576 | A | 12/1992 | Krent et al. | |
| 5,173,964 | A | 12/1992 | Ball et al. | |
| 5,222,256 | A | 6/1993 | Wang | |
| 5,445,385 | A | 8/1995 | Brooks | |
| 5,449,341 | A | 9/1995 | Harris | |
| 5,451,201 | A | 9/1995 | Prengler | |
| D364,009 | S | 11/1995 | Engdahl | |
| 5,472,769 | A | 12/1995 | Goerz, Jr. et al. | |
| 5,530,966 | A | 7/1996 | West | |
| 5,561,857 | A | 10/1996 | Hoshizaki et al. | |
| 5,594,954 | A | 1/1997 | Huang | |
| 5,623,728 | A | 4/1997 | Wagner | |
| 5,652,967 | A | 8/1997 | Hsu | |
| 5,716,120 | A | 2/1998 | Hung | |
| D396,330 | S | 7/1998 | Oetting | |
| 5,781,935 | A | 7/1998 | Bassett et al. | |
| 5,865,775 | A | 2/1999 | Peoples et al. | |
| 5,887,277 | A | 3/1999 | Lohman | |
| D407,859 | S | 4/1999 | Rule | |
| 5,921,949 | A * | 7/1999 | Dray | 602/64 |
| 5,925,010 | A | 7/1999 | Caprio, Jr. | |
| D417,036 | S | 11/1999 | Hamowy | |
| 6,035,453 | A | 3/2000 | Cain | |
| 6,059,834 | A | 5/2000 | Springs | |
| D426,678 | S | 6/2000 | Rule | |
| D430,362 | S | 8/2000 | Pagotto | |
| 6,098,196 | A | 8/2000 | Logan | |
| 6,098,208 | A | 8/2000 | Cordon | |
| 6,122,768 | A | 9/2000 | McCrane | |
| 6,128,777 | A | 10/2000 | Foreman | |
| 6,138,281 | A | 10/2000 | Chiaruttini | |
| 6,182,288 | B1 | 2/2001 | Kibbee | |
| 6,192,519 | B1 | 2/2001 | Coalter | |
| 6,205,583 | B1 | 3/2001 | Beland | |
| 6,216,268 | B1 | 4/2001 | Schleicher | |
| 6,219,843 | B1 | 4/2001 | Passi et al. | |
| 6,240,565 | B1 | 6/2001 | Spear | |
| 6,243,867 | B1 | 6/2001 | Faison | |
| 6,247,188 | B1 | 6/2001 | Beland | |
| 6,295,654 | B1 | 10/2001 | Farrell | |
| 6,328,706 | B1 | 12/2001 | Yattavong | |
| 6,374,408 | B1 | 4/2002 | Tomlinson et al. | |
| 6,398,749 | B1 | 6/2002 | Slautterback | |
| 6,503,216 | B1 | 1/2003 | Thibodo, Jr. | |
| 6,553,573 | B1 * | 4/2003 | Brown | 2/24 |
| 6,654,960 | B2 | 12/2003 | Cho | |
| 6,807,680 | B2 | 10/2004 | Sloot | |
| 6,839,910 | B2 | 1/2005 | Morrow et al. | |
| 6,880,172 | B2 | 4/2005 | Quintero | |
| 7,082,621 | B1 | 8/2006 | Fratesi | |
| 7,356,849 | B2 * | 4/2008 | Morrow et al. | 2/16 |
| 2002/0138896 | A1 | 10/2002 | Holden | |
| 2003/0028947 | A1 | 2/2003 | Fee et al. | |
| 2004/0045079 | A1 | 3/2004 | Quintero | |

OTHER PUBLICATIONS

STX Lacrosse Catalog 2000: Prototype Athletic Equipment.

* cited by examiner

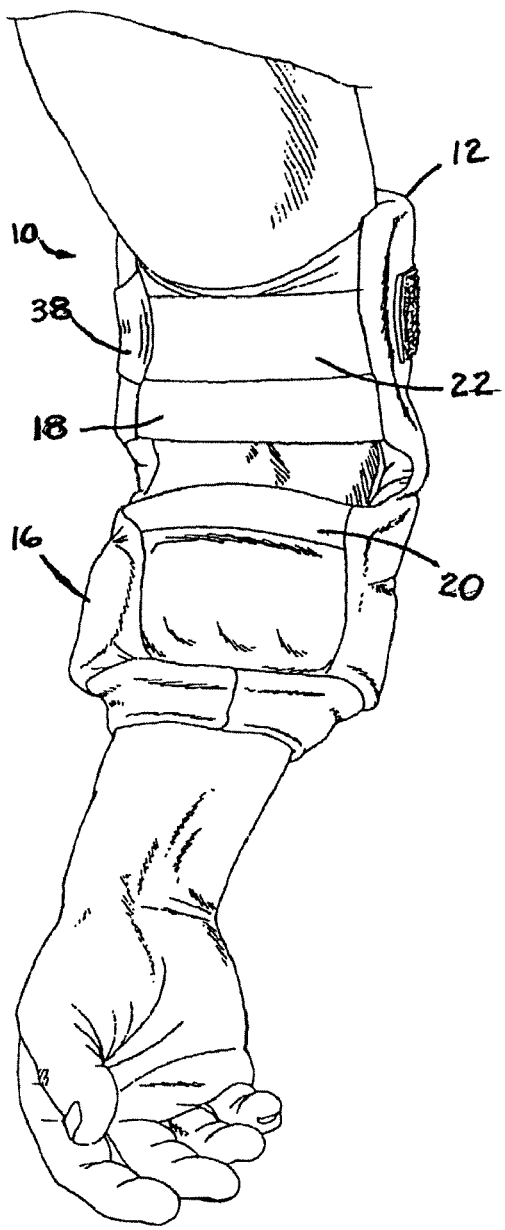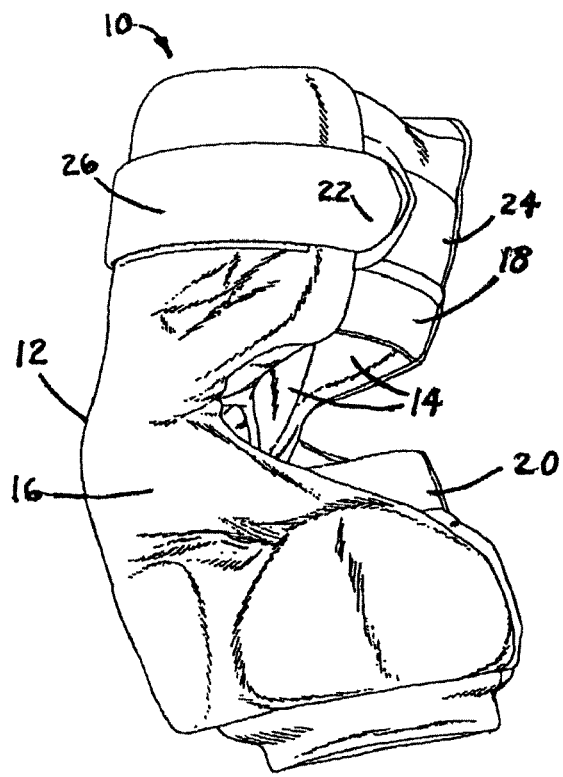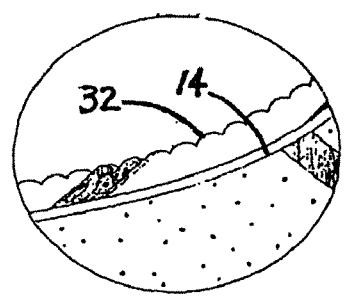

NO-SLIP PROTECTOR

CROSS-REFERENCE TO RELATED APPLICATIONS

This application is a continuation of U.S. application Ser. No. 10/187,680 for a NO-SLIP ELBOW PAD, filed Jul. 2, 2002 now U.S. Pat. No. 7,356,849.

BACKGROUND OF THE INVENTION

1. Field of the Invention

The present invention relates generally to a pad for protecting a wearer.

2. Description of Related Prior Art

It is widely known that the participants of various sports use pads and other protective gear for preventing potential injuries characteristic of the sport. For instance, a typical lacrosse player wears pads for cushioning blows normally imparted upon his arms, torso and legs such as when he is slashed by an opponent, when he falls to the ground and lands on his elbow, or when he bumps into another player. Hockey players also wear pads for protective purposes, including to cushion the impact of a fall to the ice, of hitting the boards or the goalposts, as well as to protect from injury if hit by a stick or a puck.

A typical pad includes a one piece padding element composed of a spongy energy absorbing material. The padding element covers a portion of the wearer's body.

Usually, the padding element has a pair of elastic bands that are sewn or otherwise connected to the padding element. For example, these elastic bands are typically intended to stretch against the user's upper arm and forearm for the purpose of securing an elbow pad to the participant's arm.

In an elbow pad, these elastic bands substantially stretch against the wearer's arm only while the arm is in a bent position. However, when the user's arm is straightened, the elastic bends may not be sufficiently stretched against the arm so as to secure the elbow pad in a fixed position. Consequently, the elbow pad may slide down the user's arm thereby exposing the upper arm and elbow joint to potential injury or simply causing discomfort. This sort of undesired movement typically occurs when the user repeatedly and/or forcefully bends and straightens his arms, e.g. while running or throwing a lacrosse ball or shooting or passing a hockey puck. Consequently, a user must constantly readjust the elbow pad to place it in a position for protecting the elbow joint in a manner that is comfortable to the user.

In addition, some elbow pads may include one or more adjustable straps that may further tighten the fit of the elbow pad on the user's arm. If the adjustable straps are sufficiently tightened, the elbow pad may not slide down the user's arm. However, this level of tension makes it difficult for the user to repeatedly bend his arm without an appreciable level of discomfort or exhaustion of his arm muscles.

Therefore, there is a need for a no-slip pad that provides adequate protection against injuries while the user makes sudden, forceful arm movements without the need for constant adjustment.

SUMMARY OF THE INVENTION

In summary, the invention is a protector for protecting a wearer. The protector includes a protective element extending along an axis between first and second ends. The protective element has an inner surface for at least partially contacting a wearer, an outer surface opposite the inner surface, and an outer edge. The protector also includes at least one elastic band arrangement connected to the outer edge at two places and overlaying the inner surface and being operable to allow at least a portion of the wearer to be received between the at least one elastic band and the inner surface. The protector also includes at least one friction element coupled to the inner surface and discreet from the at least one elastic band. The at least one friction element defines a greater coefficient of friction than the inner surface and is thereby more operable to minimize movement of the protection element relative to the wearer than the inner surface. The at least one friction element and the at least one elastic band are spaced from one another along the axis such that either the at least one friction element or the at least one elastic band can tend to limit sliding movement of the protective element as the portion of the wearer expands or contracts during use.

It is therefore an object of the present invention to provide a pad, which remains effectively locked in a desired position on a user's body despite sudden forceful and/or repetitious arm movements that may otherwise cause the pad to propagate down the user's body.

It is another object of the present invention to provide a pad, which stays in place and permits a user to focus his attention on an ongoing game or any other ongoing activity.

It is yet another object of the present invention to provide a pad, which has a relatively light weight for improving a user's performance in a sporting event or any other ongoing activity that requires body protection.

It is still another object of the present invention to provide a pad, which has a simple design that reduces manufacturing time and costs associated therewith.

In accordance with the above and other objects of the present invention, a no-slip pad is provided for securely fastening to a user's body and adequately protecting the user's body. The no-slip pad includes a padding element having an inner surface and an outer surface. The padding element may have two bands integrally connected thereto. These bands overlay the inner surface of the padding element and are intended to secure the no-slip pad to the user's body. The inner side has at least one friction element integrated thereon. Each friction element is intended to engage the user's body to prevent the pad from sliding out of a desired position.

One advantage of the present invention is that the no-slip pad is effectively locked in a position on a user's body, despite sudden forceful body movements.

Another advantage of the present invention is that a user will not be distracted by undesired movement of a pad or any resulting need to readjust the pad.

Yet another advantage of the present invention is that the no-slip pad is relatively light weight thereby decreasing the amount of energy a user expends on wearing the pad and allowing the user to exert more energy on other activities.

Other advantages of the present invention will become apparent when viewed in light of the detailed description of the preferred embodiment when taken in conjunction with the attached drawings and appended claims.

BRIEF DESCRIPTION OF THE DRAWINGS

Advantages of the present invention will be readily appreciated as the same becomes better understood by reference to the following detailed description when considered in connection with the accompanying drawings wherein:

FIG. 1 is a perspective view of a no-slip elbow pad worn on the arm of a user, in accordance with a preferred embodiment of the present invention;

FIG. 2 is a side view of a no-slip elbow pad, in accordance with a preferred embodiment of the present invention;

FIG. 4A is a magnified cross-sectional view of the friction element having a no-slip textured surface as shown in FIG. 4, taken within circle 4A.

DETAILED DESCRIPTION OF THE EXEMPLARY EMBODIMENT

Figure 4:
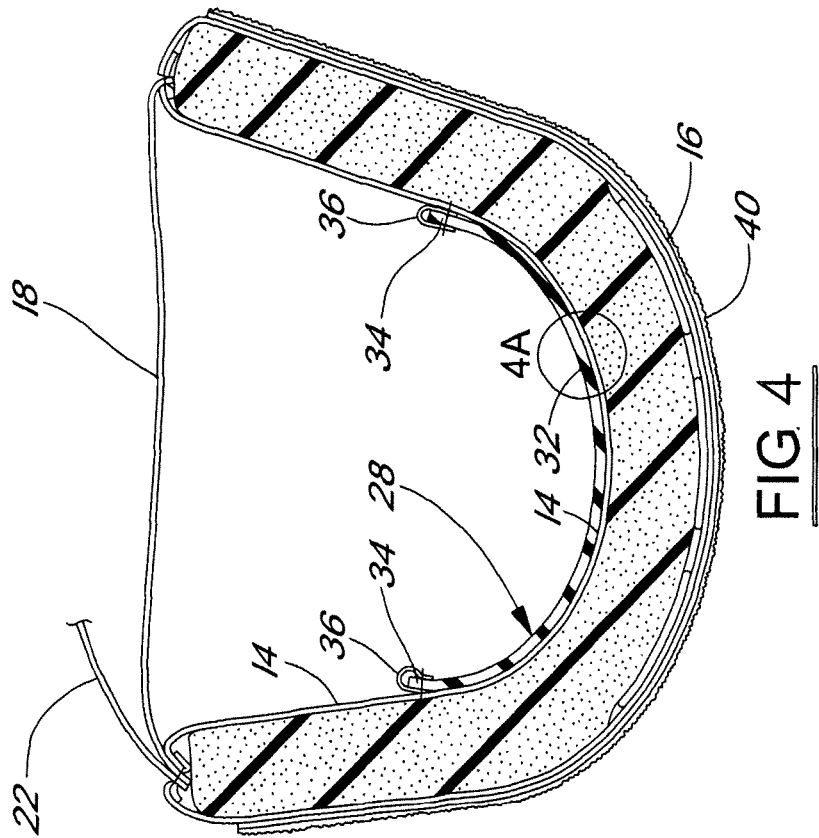
FIG. 4 is a cross-sectional view of the no-slip elbow pad as shown in FIG. 3, taken along line 4-4.

In the following figures, the same reference numerals are used to identify the same components in the various views. Also, while the exemplary embodiment of the invention is an elbow pad, pads for protecting other areas of the human body can be alternative embodiments of the invention.

Referring primarily to FIGS. 1 and 2, a no-slip elbow pad 10 is provided for protecting a user's elbow joint and the areas directly above and below the elbow joint. The no-slip elbow pad 10 includes a padding or protective element 12 having an inner lining 14 and an outer lining 16. The padding element 12 includes a plurality of arm protectors contained between the inner lining 14 and the outer lining 16. The padding element 12 extends along a longitudinal axis 50 between upper and lower ends 52, 54 with at least two edges 56, 58 disposed on opposite sides of the longitudinal axis 50.

As is known in the art, these arm protectors absorb or deflect the kinetic energy of blows delivered to the user's arm. To accomplish this, the arm protectors may be made of spongy energy absorbing materials such as foam, rigid shells, a combination thereof, or other suitable materials that protect the user's arm.

In this regard, the no-slip elbow pad 10 is beneficial to an individual performing any activity that may result in injury to his or her arm. By way of illustration, a lacrosse player may use the no-slip elbow pad 10 to protect his arm from injuries that would otherwise result when he is slashed in the arm by an opponent or when he falls to the ground and lands on his arm. The no-slip elbow pad 10 is preferably for use as an athletic protective device in sports, such as lacrosse and hockey, but may be utilized for a variety of other purposes. Moreover, while the no-slip features of the present invention are preferably applicable to elbow pads, they may also be utilized with any other type of protective equipment.

As shown, the no-slip elbow pad 10 preferably includes an upper elastic band 18 and a lower elastic band 20 for securing the no-slip elbow pad 10 to a user's arm. The upper and lower elastic bands 18, 20 are discrete from, and integrally connected with, respectively, to upper and lower portions of the padding element 12 along two edges 56, 58 of the element 12 so as to overlay the inner lining 14. The user may wear the no-slip elbow pad 10 by sliding his arm between the inner lining and the elastic bands 18, 20.

In addition to the upper and lower elastic bands 18, 20, the no-slip elbow pad 10 also preferably includes an adjustable strap 22 that tightens or loosens the fit of the elbow pad 10 on the user's arm. The strap 22 has a posterior side facing toward the inner lining 14. Preferably, the adjustable strap 22 has a first end 24 sewn or otherwise connected to the upper portion of the padding element 12. The adjustable strap 22 is preferably held adjacent to the upper portion of the padding element 12 by a ring 38 sewn or otherwise connected to the upper portion of the padding element 12.

Furthermore, the adjustable strap 22 preferably has a second end 26 with a hook fastener pad (not shown) integrated thereon. The hook fastener pad is intended to fasten to a loop pad 40 attached to the outer lining 16 of the padding element 12. However, various other kinds of opposing fasteners may be used to tighten the adjustable strap 22 at different tension levels.

The user may tighten the adjustable strap 22 to a suitable tension level for assisting the upper and lower elastic bands 18, 20 in securing and retaining the no-slip elbow pad 10 to the user's arm without causing discomfort to the user's arm or making him waste unnecessary energy in bending his arm.

Figure 3:
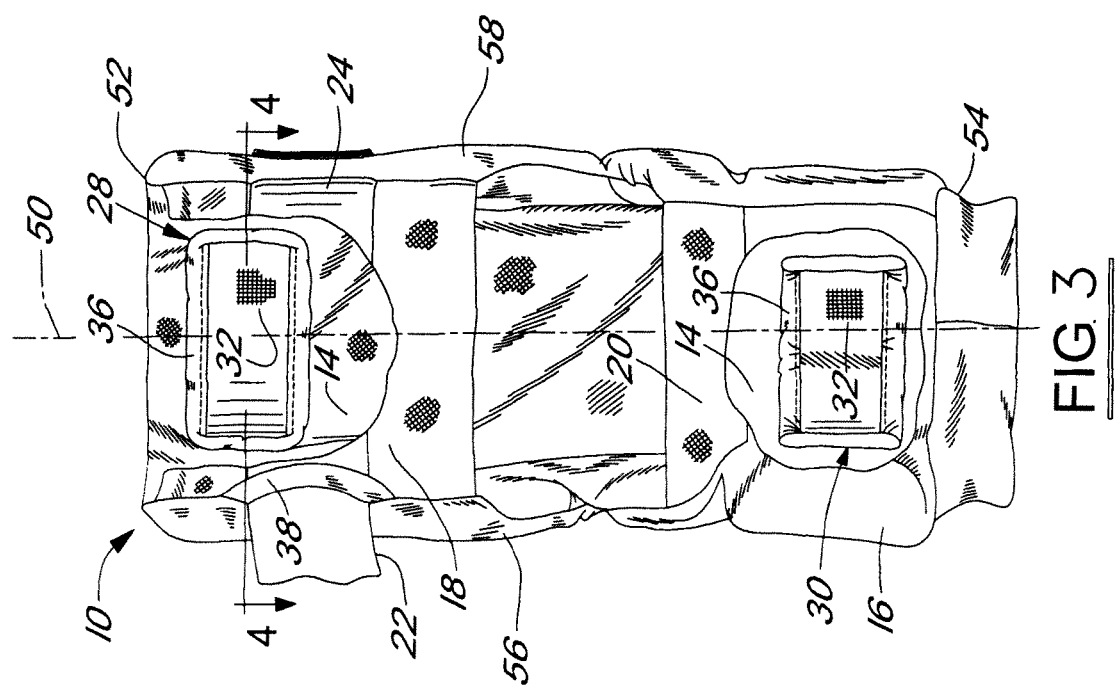
FIG. 3 is a partially cut-away front view of a no-slip elbow pad, in accordance with a preferred embodiment of the present invention.

Referring now primarily to FIGS. 3, 4, and 4A, the no-slip elbow pad 10 preferably includes an upper friction component or element 28 and a lower friction component or element 30. The friction elements 28, 30 define a greater coefficient of friction that the inner lining 14 to enhance holding of the no-slip elbow pad 10 in a desired position with respect to a wearer's arm. The exemplary elements 28, 30 are of generally rectangular shape and non-removable from the inner lining 14. Preferably, the upper and lower friction elements 28, 30 are discrete from, and integrated or connected with, respectively, on the upper and lower portions of the inner lining 14. The friction elements 28, 30 are discrete from the bands 18, 20. These upper and lower portions are in substantial contact with the user's arm when the arm is straightened. Therefore, each friction element 28, 30 is properly positioned for contacting the user's arm and preventing the no-slip elbow pad 10 from sliding out of the desired position. The friction element 28 is spaced from the band 18 along the longitudinal axis 50. The friction element 30 is spaced closer to the lower end 54 than the band 20. While two friction elements 28, 30 are disclosed, it will be understood that any number of friction pads may be utilized, including more or less than two. FIG. 4A shows that the inwardly-facing surface 32 of the friction element 30 and the inwardly-facing surface of the inner lining 14 have different textures. The surface 32 is raised and bumpy, with a repeating pattern of ridges and valleys.

Unlike the elastic bands 18, 20, these friction elements 28, 30 can easily hold the no-slip elbow pad 10 in a desired position while the user's arm is straightened. Moreover, unlike the adjustable strap 22, the upper and lower friction elements 28, 30 can effectively lock the no-slip elbow pad 10 in a desired position without causing discomfort to the user or demanding increased effort in bending the elbow pad.

Preferably, each friction element 28, 30 is comprised of a pad of neoprene rubber with a textured surface 32 for creating ample friction between the friction element 28, 30 and the user's arm. However, it is understood that each friction element 28, 30 may be made of other suitable no-slip materials that have a variety of different surface textures, including smooth surface textures. It will be understood that the friction elements 28, 30 can be constructed of any suitable material and can take on a variety of different configurations. The friction elements however are intended to create friction between the protective padding and a wearer's skin to minimize movement therebetween and thereby provide increased protection.

As best shown in FIGS. 3 and 4, each friction element 28, 30 includes a border 34 for attaching each of the friction elements 28, 30 to the inner lining 14 of the padding element 12. The border 34 is sewn or otherwise connected to the inner lining 14. However, the friction elements 28, 30 can be attached to the inner lining 14 by a variety of different attachment methods.

Furthermore, the border 34 of each friction element 28, 30 is preferably covered with a border guard 36 for reducing wear on the friction elements 28, 30. Specifically, the border guard 36 prevents each friction element 28, 30 from tearing at its border 34.

While particular embodiments of the invention have been shown and described, numerous variations and alternate embodiments will occur to those skilled in the art. Accordingly, it is intended that the invention be limited only in terms of the appended claims.

What is claimed is:

1. A protector for protecting a wearer comprising:
a protection element extending along an axis between first and second ends and having an inner surface that faces and at least partially engages a wearer in use, an outer surface opposite said inner surface and first and second outer edges, the outer surface facing away from the wearer;
at least one elastic band connected to said first and second outer edges and being operable to allow at least a portion of the wearer to be received between said at least one elastic band and said inner surface; and
at least one friction element coupled to said inner surface, said at least one friction element being separate, discrete and spaced a distance from said at least one elastic band,
wherein said at least one friction element has a greater coefficient of friction than said inner surface and is thereby more operable to minimize movement of said protection element relative to the wearer than said inner surface,
wherein said at least one of the at least one friction element and the at least one elastic band tend to limit sliding movement of the protection element as the portion of the wearer moves during use,
wherein said at least one friction element directly engages the wearer during use to limit the sliding movement of the protection element, and
wherein at least a portion of the inner surface directly engages the wearer during use.

2. The protector of claim 1 wherein said at least one friction element and said at least one elastic band arrangement are spaced from one another along said axis such that said at least one elastic band arrangement does not overlay any of said at least one friction element.

3. The protector of claim 1 wherein:
said at least one friction element includes first and second friction elements;
said at least one elastic band arrangement includes first and second elastic bands; and
wherein said first and second elastic bands are spaced closer to one another along said axis than said first and second friction elements are spaced to one another.

4. The protector of claim 1 wherein said at least one friction element is further defined as being non-removable with respect to said inner surface, and wherein said at least one friction element is secured to said inner surface such that it is not movable with respect to said inner surface.

5. The protector of claim 1 wherein said at least one friction element has an inwardly-facing surface that contacts the wearer and defines a first texture, wherein said inner surface defines a second texture different than said first texture.

6. The protector of claim 1 wherein said at least one friction element is a plurality of neoprene rubber friction elements, each spaced distal from one another, adjacent the inner surface, and wherein said at least one elastic band includes a plurality of elastic bands spaced out along said axis.

7. The protector of claim 1 wherein said at least one friction element is located substantially entirely on said inner surface of said protection element and does not extend to said first or second outer edges or to said outer surface of said protection element.

8. The protector of claim 1 wherein said at least one friction element is sewn to said inner surface.

9. A pad for engagement with a wearer's arm comprising:
a protection element that engages a wearer's arm and covers a wearer's elbow, said protective element having an inner side that faces toward the wearer's arm in use, an outer side facing outwardly, away from the wearer, and at least one protector member disposed therebetween;
at least two elastic bands fixedly joined with said protective element, said at least two elastic bands allowing a wearer's arm to slide between said inner side and an underside of said at least two elastic bands to retain said protective element in position on the wearer's arm;
at least one no-slip element non-removably secured to said inner side to minimize movement of the pad with respect to said wearer's arm, said at least one no-slip element being separate, discrete and spaced a distance from said at least two elastic bands, said no-slip element including a border defining an outer perimeter of said no-slip element, said at least one no-slip element secured to said inner side such that said border is stationary with respect to said inner side,
wherein said no-slip element and said inner side define coefficients of friction such that said no-slip element coefficient of friction is greater than said inner side coefficient of friction,
wherein said at least one no-slip element contacts the wearer's skin during use, and
wherein the inner side contacts the wearer's skin during use.

10. The pad of claim 9 wherein said at least one no-slip element is constructed of a neoprene material.

11. The pad of claim 9 wherein said at least one no-slip element is further defined as at least two no-slip elements separated a distance from each other and secured to said inner side of said protective element, wherein a first no-slip element contacts the wearer's arm above the elbow, and wherein a second no-slip element contacts the wearer's arm below the elbow.

12. The pad of claim 9 wherein said at least one no-slip element has a raised textured surface.

13. The pad of claim 9 wherein said at least one no-slip element is generally rectangular in shape.

14. A pad for engagement with a wearer's arm comprising:
a protective element intended to engage a wearer's arm and cover a wearer's elbow, said protective element having an inner surface that faces toward a wearer's arm in use; an outer surface facing away from the wearer's arm; and at least one impact resistant member disposed therebetween;
at least one elastic band fixedly secured to said protective element and facing said inner surface, said at least one elastic band allowing a wearer's arm to slide between said inner surface and an underside of at least one elastic band to retain said protective element on said wearer's arm;
at least two no-slip friction elements, which are separate and discrete from said at least one elastic band, said at least two no-slip friction elements being separated a distance from each other a preselected distance and fixedly secured to said inner surface to minimize movement of the pad with respect to the wearer's arm,
wherein said at least two no-slip friction elements face toward and contact the wearer's arm, wherein said at least two no-slip friction elements and said inner surface define coefficients of friction such that said at least two no-slip friction elements each define a greater coefficient of friction than said inner surface and are thereby more operable to minimizing movement of the pad on the arm of the wearer than said inner surface.

15. The pad of claim 14 comprising:
an adjustable strap to assist in adjusting the fit of said protective element to said wearer's arm, said adjustable strap secured to said protective element, but distal from and unjoined with said at least two no-slip friction elements.

16. The pad of claim 14, wherein said at least one elastic band a first elastic band disposed adjacent an upper arm portion of said protective element and a second elastic band disposed adjacent a lower arm portion of said protective element.

17. The pad of claim 14, comprising at least two elastic bands each separated from one another a distance along a longitudinal axis of the protective element, each adapted to engage different portions of the wearer's arm.

18. The pad of claim 14, wherein said at least two no-slip friction elements are fixedly secured to said inner surface adjacent said upper arm portion.

19. The pad of claim 14, wherein said at least two no-slip friction elements are constructed of a rubber material.

20. The pad of claim 19, wherein said at least two no-slip friction elements are constructed of a neoprene material.

21. The pad of claim 14, wherein a plurality of no-slip friction elements are secured substantially entirely to said inner surface of said protective element, such that said no-slip friction elements do not extend to said outer surface of said protective element.

22. The pad of claim 21, wherein said at least two no-slip friction elements are attached to said inner surface, about the perimeter of said no-slip friction elements, such that no portion of the perimeter of said friction elements are movable with respect to said inner surface.

23. The pad of claim 14, wherein said at least two no-slip friction elements are generally rectangular in shape.

24. A protective pad for engagement with a wearer's arm comprising:
a protective portion for engaging a wearer's arm, said protective portion having an inner surface that faces toward and at least partially contacts a wearer in use, and an outer surface, opposite said inner surface, said outer surface facing outwardly away from the wearer, said outer surface adapted to directly contact at least one of the ground and another surface during use, said protective portion having a first side and a second side;
a plurality of elastic bands secured to said protective portion and facing said inner surface, said plurality of elastic bands allowing a wearer's arm to pass between said inner surface and an underside of said plurality of elastic bands to retain said padded portion to said wearer's arm; and
a plurality of friction elements being non-releasably secured to said inner surface, said friction elements and said inner surface each having a surface texture, said surface texture of said friction elements being different from said surface texture of said inner surface to minimize movement of the pad with respect to said wearer's arm, said friction elements located substantially entirely on said inner surface and not extending to said outer surface or said first or second sides of said protective portion;
wherein said plurality of friction elements are secured to said inner surface such that substantially all of said friction elements are immovable with respect to said inner surface,
wherein said plurality of friction elements are separate and discrete from said inner surface and said plurality of elastic bands, and
wherein said plurality of friction elements and at least a portion of the inner surface of said protective portion contact the wearer's skin during use.

\* \* \* \* \*